United States Patent [19]

Schultz

[11] Patent Number: 5,281,134
[45] Date of Patent: Jan. 25, 1994

[54] FIBER OPTIC ILLUMINATION SYSTEM FOR DENTAL INSTRUMENTS

[76] Inventor: Allen J. Schultz, 7682 E. Cedar Creekway, Orange, Calif. 92669

[21] Appl. No.: 794,427

[22] Filed: Nov. 19, 1991

[51] Int. Cl.$^5$ ............................................. A61C 3/00
[52] U.S. Cl. ........................................ 433/29; 433/31; 433/91
[58] Field of Search ................ 433/29, 31, 91, 92, 433/93, 94, 95, 96

[56] References Cited

U.S. PATENT DOCUMENTS

| | | | |
|---|---|---|---|
| 50,461 | 10/1865 | Dibble | 433/93 |
| 2,823,455 | 2/1958 | Sprague | 433/31 |
| 2,861,342 | 11/1958 | Katz | 433/31 |
| 3,614,415 | 10/1971 | Edelman | 433/93 |
| 3,758,951 | 9/1973 | Scrivo et al. | 433/29 |
| 4,562,832 | 1/1986 | Wilder et al. | 128/18 |
| 4,592,344 | 6/1986 | Scheer | 433/29 |
| 4,629,425 | 12/1986 | Detsch | 433/31 |
| 4,704,660 | 11/1987 | Robbins | 362/32 |
| 4,883,426 | 11/1989 | Ferrer | 433/93 |
| 4,915,626 | 4/1990 | Lemmey | 433/29 |
| 4,986,622 | 1/1991 | Martinez | 128/4 |
| 4,992,047 | 2/1991 | Warner | 433/91 |

FOREIGN PATENT DOCUMENTS

1349227  4/1974  United Kingdom ................... 433/29

OTHER PUBLICATIONS

"Eska High-performance Plastic Optical Fibers", by Mistubishi Rayon Co., Ltd., Product brochure.
"Improved Visibility for Surgical Procedures with Fiber Optics" by Zeza, Inc., Product brochure.
Product brochure by Quality Aspirators.

Primary Examiner—John J. Wilson
Attorney, Agent, or Firm—Hawes & Fischer

[57] ABSTRACT

A fiber optic illumination system for dental instruments of the present invention enables a light source to provide light to the oral cavity using a single continuous polymethyl methacrylate optical fiber axially fitted into a cylindrical tube, open at both ends, and affixed to a dental instrument, such as a mirror, aspirator, or retractor, for example. The end of the cylindrical tube and the inserted portion of the single continuous polymethyl methacrylate optical fiber it supports contacts the fluids in the oral cavity. After treatment, the end of the single continuous polymethyl methacrylate optical fiber is removed from the cylindrical tube and immersed into a 1:4 glutaraldehyde, or equivalent, solution and subsequently wiped clean. The dental instrument and attached cylindrical tube, now devoid of optical fibrous material, is completely and fully sterilized in a normal fashion, such as by autoclaving.

20 Claims, 6 Drawing Sheets

FIBER OPTIC ILLUMINATION SYSTEM FOR DENTAL INSTRUMENTS

BACKGROUND OF THE INVENTION

The present invention relates to an improved appliance for use in conjunction with dental instruments to illuminate the oral cavity during the performance of dental work. The invention particularly relates to the design and use of an illumination system which enables quick separation of the fiber optic portion of the illuminator for cold liquid sterilization while enabling the dental instrument to be sterilized in a conventional fashion.

The use of fiber optic illumination in conjunction with dental treatment is well known. One of the prime objectives in providing illumination to the oral cavity is the elimination eye fatigue. An assistant can also independently direct a light source if desired Examples include U.S Pat. No. 3,614,415 to Edelman, entitled "Fiber Illuminator", U.S. Pat. No. 4,992,047 to Warner, entitled "Surgical Suction Tool", U.S. Pat. No 4,986,622 to Martinez, entitled "Fiber Optic Light Transmission Apparatus", and U.S. Pat. No. 4,704,660, to Robbins, entitled "High-Intensity Light Source for a Fiber Optics Illumination System."

Another system for fiber optic illumination is a clip on system made by Quality Aspirators of Duncanville, Tex. The scheme employed there includes a clip-on wand having an illuminating end opposite a compound curved connector end. The curve is for the purpose of mounting along the upward end of the dental instrument while allowing the fiber optic connector and its lead in cable to hang below the dental instrument.

This is an example of known schemes which involve the use of a number of glass fibers to transmit light from a light generator to a point proximate to a dental instrument. The light is further propagated and coupled into a rigid encased light guide within a cavity provided in a dental instrument. Typically the optic fiber bundle or fiber is epoxied or otherwise permanently encased or "potted" into a tube which is attachably held in place with respect to the dental instrument by solder or clips.

The point of connection between the rigid, encased light guide and the flexible fiber optic fiber or bundle always involves some difficulty. If the impedance match of the connection is not sufficiently good, significant amounts of light will be reflected from the point of connection back to the light source. This will cause a more intense light source to be required in order to deliver the same level of light to the illuminated area given the percentage reflection. Further, the excess light reflectively propagating in the volume between the flexible fiber optic bundle and the rigid encased guide representing a loss, will be converted to heat, potentially making the instrument uncomfortable to use.

The tube encasing the rigid light guide is closed at one end with a transparent cap or lens to couple and adjust light from the rigid light guide into the area to be illuminated. The sealing of the end of conventional fiber optic illuminators is important for several reasons. First, non-sterile liquids, such as saliva and blood could be wicked into the area between the rigid light guide and the tube encasing it by capillary action. This is particularly true where the rigid light guide is a fiber optic bundle, and additional wicking may occur between the fibers in the bundle.

Secondly, exposing the rigid light guide optical fibers directly into the oral cavity would cause their light transmissive properties to degrade due to the scoring to which the ends of the fiber would be subjected over time. However, the sealing of the end of the tube, and the fixing of the rigid light guide within the tube causes problems associated with sterilization. Once the dental instrument, including the tube encasing the rigid optical fibers has been used in the dental environment, it becomes necessary to sterilize the contaminated portions.

Since the fiber optic light guide is permanently encased within its supporting tube they must be sterilized together. High temperatures cause epoxy to break down and turn yellow in a short time period. A rigorous sterilization involving strong chemicals and high temperature for the instrument is also a rigorous sterilization for the encased rigid light guide. Exposure of the end of the tube connected to the flexible optical fiber to chemicals tends to harm the optical fibers, reducing the ability of the flexible fibers to transmit light into the rigid light guide. Further, exposure to other sterilization techniques causes degradation of the epoxy which holds the rigid light guide in place.

Further, repeated exposure of the rigid light guide optical fiber to high temperatures causes reduction of its light transmission characteristics throughout its volume. Light transmitted into the flexible optical fiber is energy, and any light not reaching the oral cavity for illumination there is expended elsewhere in the form of heat if not allowed to escape in the form of light. As the rigid light guide's ability to transmit light decreases, it absorbs light causing it to heat up. The heat is transmitted into the tube encasing the fiber and causes the tube and the dental instrument to become uncomfortably hot. As the light energy is absorbed in the instrument, the illumination level in the oral cavity becomes insufficient.

Further, the cost of manufacture of the conventional dental illumination system outlined above is expensive, both in terms of the rigid light guide within the dental instrument, as well as in terms of the flexible light guide used for transmitting light to the dental instrument, and especially the connector used to join the two light guides.

Illumination of the oral cavity can be accomplished by the use of fiber optics. However, what is needed is a system which will allow such illumination to take place inexpensively, which will not present an impediment to sterilization, either from reluctance to perform a full sterilization of the dental instruments in contact with the oral cavity to prevent harm to the fiber optic portions, or from a design not inhibitive of a full sterilization.

Further, a system is needed which will operate with as few points of loss as possible. The needed system should also be as efficient as possible, such that adequate light may be supplied with a low cost in terms of energy into the system. The geometry of such a low cost, efficient system should ensure complete sterilization, and enable adequate visual inspection of all areas where unsanitary contamination might exist.

BRIEF SUMMARY OF THE INVENTION

The fiber optic illumination system for dental instruments of the present invention enables a light source to provide light to the oral cavity using a single continuous polymethyl methacrylate optical fiber. A cylindrical tube, open at both ends is affixed to a dental instrument, such as a mirror, aspirator, or retractor, for example. The end of the single continuous optical fiber, which may be stripped of its outer protective sleeve, is inserted into the end of and axially through the cylindrical tube until the end of the optical fiber reaches a point near the end of the cylindrical tube nearer the end of the dental instrument opposite its handle.

The end of the cylindrical tube and the inserted portion of the single continuous polymethyl methacrylate optical fiber it supports is allowed to come into contact with the fluids in the oral cavity. After treatment is concluded, the end of the single continuous polymethyl methacrylate optical fiber is removed from the cylindrical tube and immersed into a 1:4 glutaraldehyde, or equivalent solution for a time period specified by the manufacturer, before being dried. The dental instrument and attached cylindrical tube, now devoid of optical fibrous material, is completely and fully sterilized in a normal fashion. Such sterilization may be accomplished with any combination of heat and active chemicals to insure a complete sterilization.

Further, the illumination system of the present invention facilitates the use of fiber optic illumination as a retro-fittable option on dental instruments not originally provided with fiber optic illumination. The physical configuration of the illumination system of the present invention does not depend upon cooperating allowances in the configuration of the dental instrument to which it is attached.

BRIEF DESCRIPTION OF THE DRAWINGS

Other aspects, features and advantages of the invention, its configuration, construction, and operation will be best understood from the following detailed description, taken in conjunction with the accompanying drawings in which:

FIG. 3b is a front view of the retainer ring shown with the retractor of FIGS. 3 and 3a.

DETAILED DESCRIPTION OF THE PREFERRED EMBODIMENT

Figure 1:
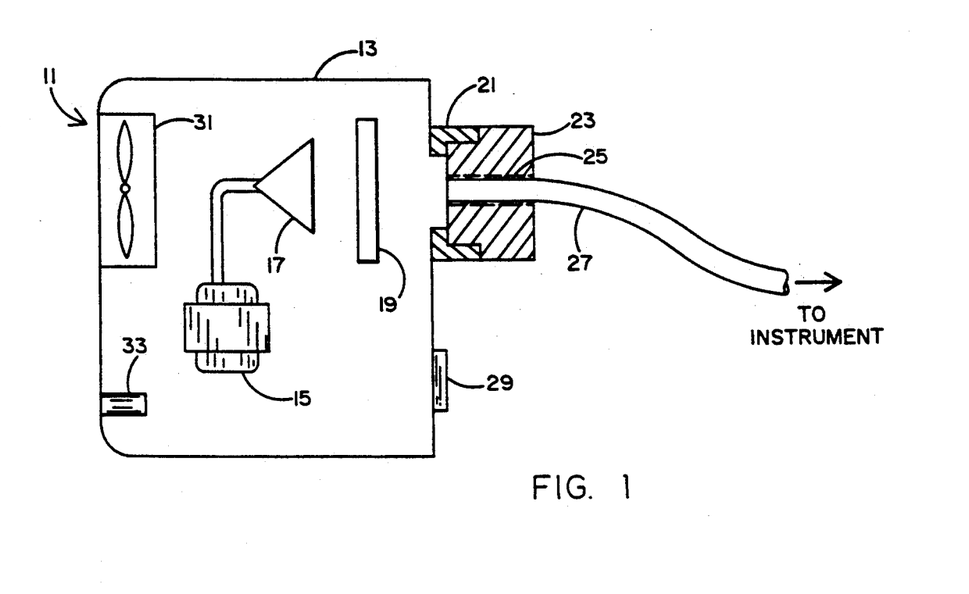
FIG. 1 illustrates a top view of light source for the fiber optic illumination system of the present invention.

Referring to FIG. 1, a light source system 11 of the present invention is illustrated in top view. Within a boundary 13 of the light source system 11 is a transformer 15 connected to supply electrical power to a lamp 17. Lamp 17 may be a 150 watt 21 volt lamp, or similar, sufficient to supply an adequate amount of light into the fiber optic illumination system of the present invention for enhancing the ability to provide dental treatment.

A tempered heat absorbing glass 19 is positioned in front of lamp 17 in order to block the transmission of radiant heat energy through absorbing glass 19, yet permitting visible light energy to pass through heat absorbing glass 19. A fitting 21 is positioned on the opposite said of heat absorbing glass 19 to which is directed the visible light transmitted through heat absorbing glass 19.

Into fitting 21 is positioned an adapter 23. Adapter 23 surrounds the end of a single, or monofilament, light guide 25. Light guide 25 is typically a polymethyl methacrylate optical fiber, such as the type manufactured and sold by Mitsubishi Rayon Co., Ltd under the trade name ESKA ™. This fiber light guide 25 has a concentric double-layer structure consisting of a core of highly transparent polymethyl methacrylate polymer and a thin layer of special fluorine polymer cladding having a lower refractive index than the core. Such a fiber light guide 25 will typically have other desirable characteristics such as flexibility, resilience, toughness and non-sensitivity to its environment. In addition, light guide 25 will also typically have a protective sheath 27 to protect its outer fluorine polymer cladding from nicks and wear.

The boundary 13 of the light source system 11 also includes an on/off switch 29. A fan 31 provides ventilation to the components within the boundary 13 to prevent overheating. A fuse 33 is provided as a safety precaution against the possibility of over current failure, as is typical with respect to electrically driven devices.

It is understood that the tempered heat absorbing glass 19 is but one method of limiting radiant heat from reaching the end of the end of the light guide 25. Limiting the heat is an important factor since the polymethyl methacrylate polymer and thin layer of special fluorine polymer cladding are known to withstand a maximum service temperature of about 80 centigrade. The other methods for limiting the heating of the light guide 25 include cooling, through the use of extended area heat rejection surfaces, as well as the use of a coolant, such as water.

Figure 2:
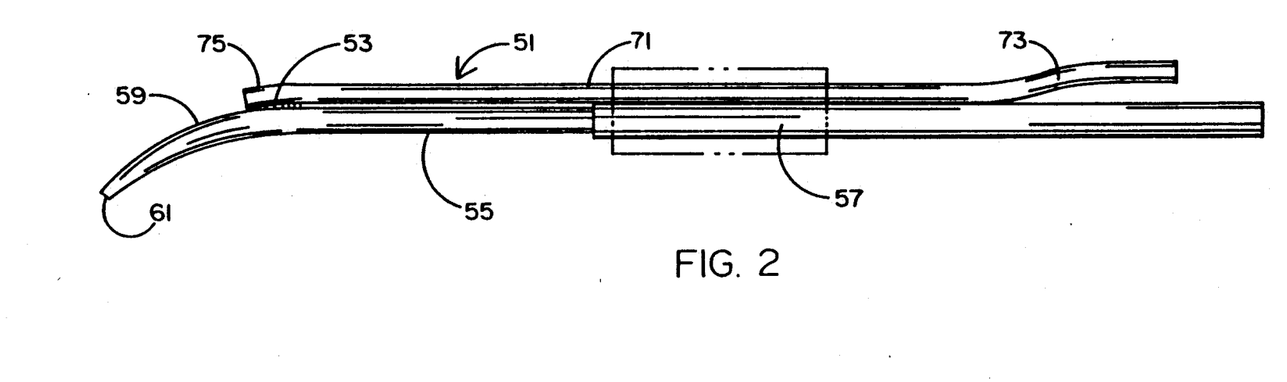
FIG. 2 is a side view of a simple aspirator utilizable in conjunction with the fiber optic illumination system for dental instruments of the present invention.

Referring to FIG. 2, an aspirator 51 is generally a hollow tube having a slight bend 53 near one end. Aspirator 51 has a forward tubular portion 55 made of 3/16 inch outer diameter tubing having a 0.020 inch thick wall, and a rearward tubular portion 57 made of ¼ inch outer diameter tubing having a 0.28 inch thick wall. A tip end 59 may be tapered and has an opening 61 which is illustrated as being angled with respect to the axis of the tip end 59. The operation of the aspirator 51 is typically accomplished by attaching the rearward tubular portion 57 to a suction tube, and bringing the tip end 59 into contact with a wetted portion of the oral cavity during dental surgery.

At the top portion of aspirator 51, a cylindrical tube 71 is attached. The manner of attachment may be by soldering, brazing or tack welding. Cylindrical tube 71 has a shallow "s" shaped bend 73 near one end, and a slight bend 75 near the tip end 59 of the aspirator 51, generally congruent with the shape of the portion of aspirator 51 to which it is adjacent. This "s" shaped bend places friction on the light guide 25 so that it will stay in place. However, firm longitudinal force will enable the withdrawal of the light guide.

Figure 3:
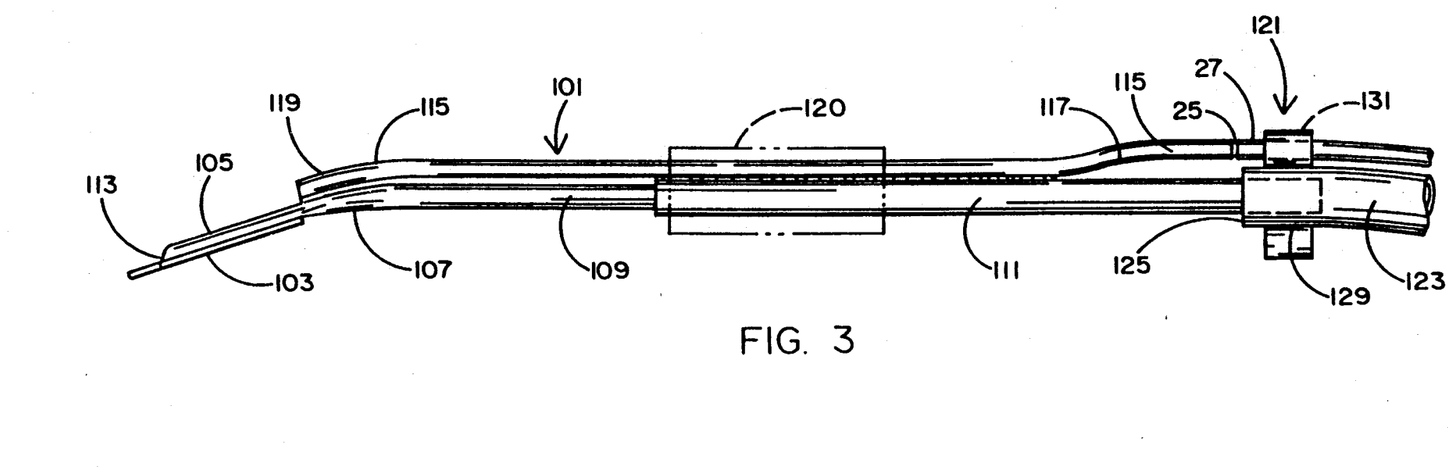
FIG. 3 is a side view of an aspirative retractor, and fitted for utilization in conjunction with the fiber optic illumination system for dental instruments of the present invention.
Figure 3A:
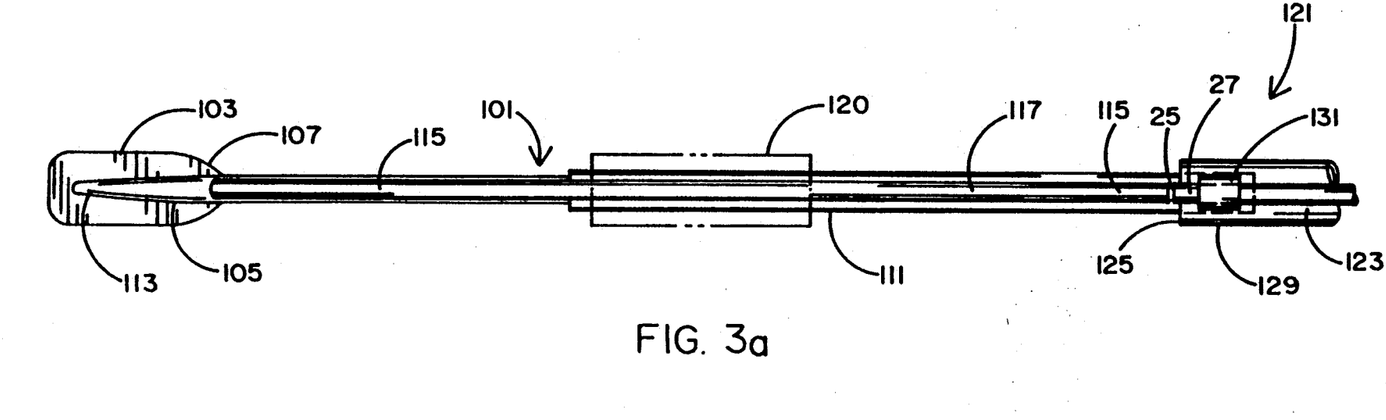
FIG. 3a is a top view of the retractor of FIG. 3.
Figure 3B:
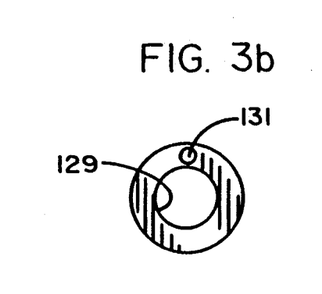

Referring to FIGS. 3, 3a and 3b, an aspirator 101 similar to the aspirator 51 of FIG. 2 has a retractor blade 103 mounted near its tip 105. The two preferred blade 103 sizes are 11 and 16 millimeters wide. The tip 105 is "set back" from the end of the blade 103 varying distances, in order to control the "V" shape created by the blade 103 at the retraction site.

Similar to retractor 51, retractor 101 has a slight bend 107, a forward tubular portion 109, a rearward tubular portion 111, an opening 113, a cylindrical tube 115 mounted on its top side including an "s" bend 117, and a slight bend 119. The slight bend 119 partially follows the bend of the aspirator tip 105, which is provided with a 15° bend to allow more universal access to the tissues of the oral cavity. Opening 113 is slightly beveled with respect to the axis of the tip 105 to reduce air flow noise. Further, the bevel allows the treatment provider to convert from a general field suction, to side specific suction by simply rotating the retractor 101 to cause the bevel to contact the operative site. Further, the retractor 101 may be fitted with a silicone band 120 surrounding both cylindrical tube 115 and at least one of the forward and rearward tubular portions 109 and 111 respectively. Silicone band 120 is heat resistant, and may be sterilized in an autoclave along with the retractor 101.

Attached to the rearward tubular portion 111 is a fitting 121, including a length of vinyl or silicone, suction tubing 123 terminating in an end 125. About the outer periphery of tubing 123, and adjacent the end 125 is a retainer ring 127. Retainer ring 127 is preferably a polymer that can resist sterilization such as Teflon or Delron ® type. Retainer ring 127 has a concentric bore 129 to accommodate tubing 123 and an offset bore 131 to accommodate light guide 25. A plurality of retainer rings 127 may be positioned along tubing 123 to support light guide 25 adjacent tubing 123.

Light guide 25, including its cladding 27, is typically affixed within bore 129 of retainer ring 127 as is tubing 123 affixed within bore 131. Note that the cladding 27 terminates at a point just beyond retainer ring 127, exposing the inner and outer core of the light guide 25 just before light guide 25 enters cylindrical tube 115.

Light guide 25 is held in place within cylindrical tube 115 by several aspects of the design of the present invention. The "s" bend 117 and slight bend 119 increase the friction against the inside of the cylindrical tube 115 by the light guide 25 to militate against its being axially pulled out while being used by the operator. The tubing 123 is friction fit onto the rearward tubular portion 111 of retractor 101. The closeness and parallel nature of tubing 123 with respect to light guide 25 cause the friction fit of light guide 25 within cylindrical tube 115 and the friction fit of tubing 123 onto the rearward tubular portion 111 of retractor 101 to mutually reinforce each other to inhibit removal of fitting 121 from retractor 101.

Figure 4:
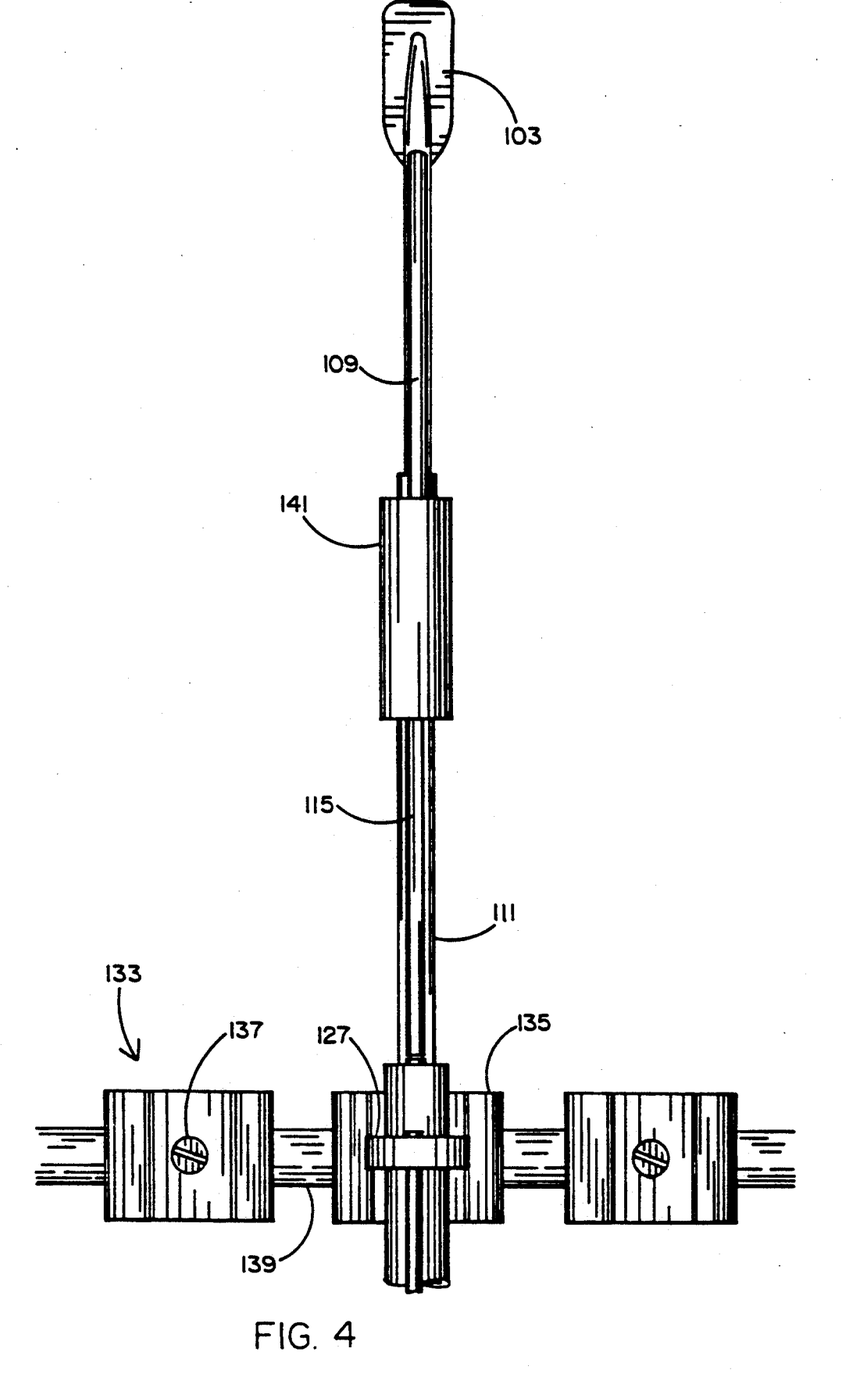
FIG. 4 is a top view of the fiber optic illumination system for dental instruments utilized in conjunction with an aspirator having a retractor blade as shown in FIGS. 3 and 3a, but shown mounted in a storage rack utilizable in conjunction with the fiber optic illumination system for dental instruments of the present invention.

FIG. 4 illustrates the bladed aspirator of FIG. 3 mounted in a storage rack 133. Retainer ring 127 is utilized in conjunction with a sectional holder ring 135. Holder ring 133 has a portion of its circumference removed sufficient to permit the retractor 101 to be moved laterally within its radius. However, enough of its circumference is present to engage and retain the retainer ring 127, once the retainer ring is moved axially downward within the inner periphery of the holder ring 135.

In the rack 133, each holder ring 135 is held in place by a screw 137 oriented transverse to the axis of the holder ring 135. Each screw 137 is secured by an aluminum strip 139. Aluminum strip 139 is configured to support a plurality of dental instruments, such as retractor 101, by its retainer ring 127. In FIG. 4, retractor 101 is shown fitted with a silicone band 141 positioned appropriately to assist in the manual use of retractor 101. Silicone band 141, like band 120, increases the comfort in using retractor 101 and enables a readily findable axial position for holding the retractor 101. Silicone band 141 is a high temperature material which stays with the retractor 101 during sterilization, which is performed conventionally.

The operation of the bladed retractor 101 of FIG. 3 is identical to that for the non-bladed retractor of FIG. 2, and is as follows. Before the dental procedure, fitting 121 is brought into proximity with the sterilized retractor 101. First, the length of light guide 25 having its protective sheath 27 removed is inserted into the end of cylindrical tube 115. The light guide 25 is inserted past both the "s" bend 117 and the slight bend 119 as the end of tubing 123 is brought into proximity to the rearward tubular portion 111 of retractor 101. The end of tubing 123 is then fitted over the end of the rearward tubular portion 111 of retractor 101, bringing the end of the protective sheath 27 into its closest proximity to the cylindrical tube 115.

Light guide 25 sits either flush with or slightly recessed from the tip 105 end of cylindrical tube 115. In this manner, the light from the end of light guide 25 will be more directed into the oral cavity under treatment rather than toward the treatment provider. During treatment, it is expected that contaminated liquids may enter the annular space between the exterior of optical fiber 25 and the interior of cylindrical tube 115. Such entry may occur through capillary action, and may depend upon the size of the annular clearance.

After treatment, instruments are debridled and then immersed in the solution for a time period prescribed by the manufacturer to effect the desired "kill" of bacteria and viruses. The fitting 121 is removed from the retractor 101, and exposed to a 1:4 glutaraldehyde solution or its equivalent by immersion for a specific time period. The portions of the retractor 101 remaining after removal of the fitting 121 are sterilizeable in a normal manner, as by total immersion in a cold steriliant, heating, autoclaving, etc. Since the exposed end of the light guide 25 is solid and contains no crevices or capillary volumes, it is not susceptible to the transmission of contaminated matter from one patient to another. During immersion all contaminants are destroyed. Alternatively, the light guide 25 is inexpensive enough to be discarded after a single use, if contamination of the fiber was of a more serious concern.

Figure 5:
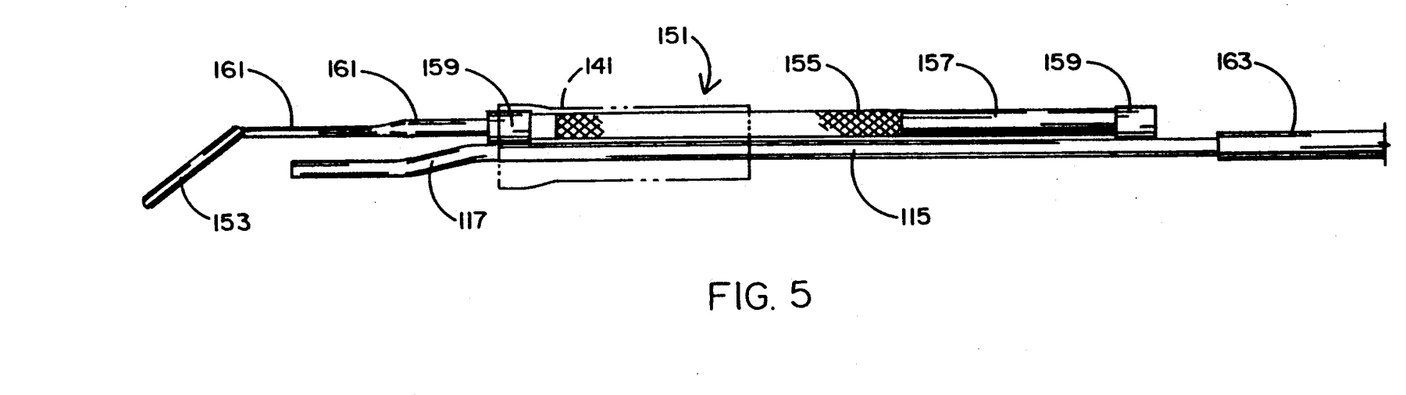
FIG. 5 is a side view of the fiber optic illumination system for dental instruments utilized in conjunction with a simple dental mirror utilizable in conjunction with the fiber optic illumination system for dental instruments of the present invention.

Further embodiments of the fiber optic illumination system for dental instruments will be illustrated with respect to the remaining Figures. FIG. 5 is a side view of a dental mirror 151 with cylindrical tube 115 oriented to illuminate the mirror 151's reflective surface 153. Mirror 151 has a knurled portion 155 of its main shaft 157 partially covered by the silicone band 141 which was illustrated in FIG. 4. Knurled portion 155 assists in frictional contact with the silicone band 141. Mirror 151 further has forwardly and rearwardly located lands 159 at the ends of the main shaft 157, and a support 161 extending from beyond one of the lands 159.

Mirror 151 has many of the same structures associated with retractor 101, including cylindrical tube 115, "s" bend 117. Here, the cylindrical tube is attached to the lands 159 at either end of the main shaft 157. In this manner, the support 161, main shaft 157, and reflective surface 153 may rotate together with respect to the lands 159 which are attached to cylindrical tube 115. Here, rotation occurs for 360°, and both into and out of alignment with the end of the cylindrical tube 115 so that the dental mirror 151 can be used for either indirect or direct vision and illumination. Further, rotation of the reflective surface 153 will facilitate the use of mirror 151 by both left and right hand operators.

Again, the manner of attachment of cylindrical tube 115 to the lands 159 of mirror 151 may be by any appropriate means, such as brazing, soldering or welding.

At the end of cylindrical tube 115 is positioned an expanded diameter portion 163. Generally, the internal diameter of expanded diameter portion 163 will match the outer diameter of cylindrical tube 115 so as to fit over it. Expanded diameter portion 163 is for the purpose of assisting in the manual insertion of the light guide 25 into the cylindrical tube 115 by first causing it to pass through a slightly larger diameter opening. While in the larger diameter portion 163, the light guide 25 will be somewhat more aligned with the internal diameter of larger diameter portion 163 than it would other wise would be without the use of larger diameter portion 163. Large diameter portion 163 has a rounded outer edge to provide strain relief at the point of entry of the light guide 25. A sharp edged point of entry may tend to subject light guide 25 to damage. Also, a large diameter portion 163 telescopes into retainer ring 127 so that it can be stored vertically.

Figure 6:
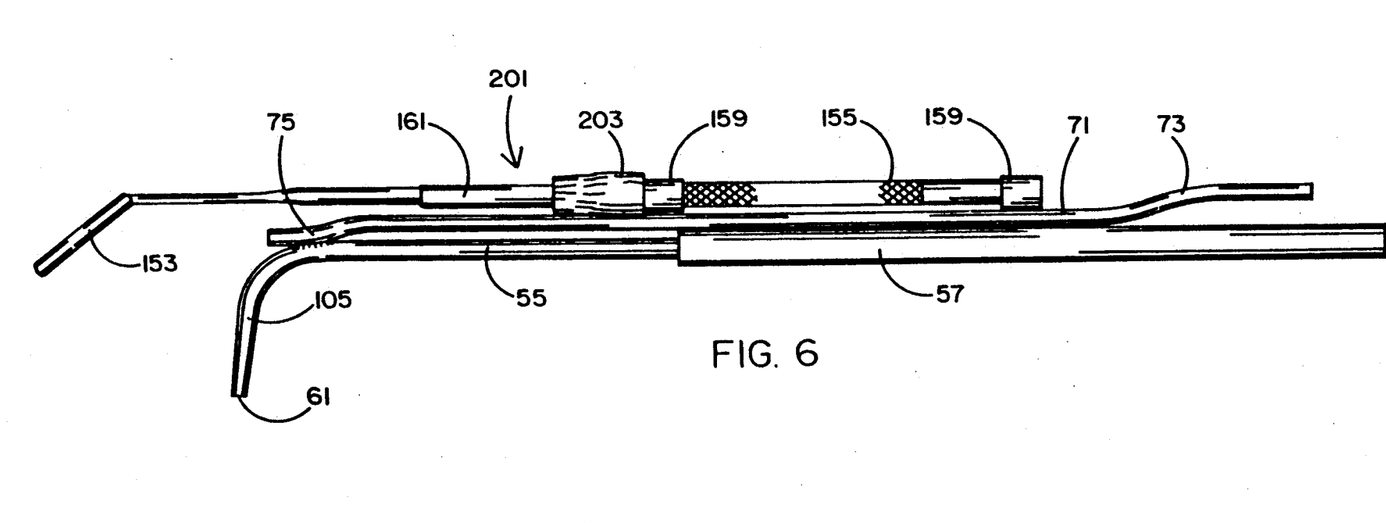
FIG. 6 is a side view of the fiber optic illumination system for dental instruments utilized in conjunction with a combination dental mirror-simple aspirator utilizable in conjunction with the fiber optic illumination system for dental instruments of the present invention.

Referring to FIG. 6, a combination aspirator-mirror instrument 201 is illustrated. The aspirator which was shown in FIG. 2 is fitted with the cylindrical tube 71 in the same manner as was shown in FIG. 2. Cylindrical tube 71 has the slight bend 75 and the "s" bend 73, which was illustrated in FIG. 2. Further, the other side of cylindrical tube 71 is attached to dental mirror 151 in a manner as was shown in FIG. 5. Here, the dental mirror 151 is enabled to rotate, as was the case in FIG. 5. Combination aspirator-mirror instrument 201 allows rotation of the reflective surface 153.

A small tubular piece of silicone plastic or rubber 203 surrounds the extended support 161, and somewhat frictionally engages the cylindrical tube 71 to provide some pivotal resistance to the pivoting of the extended support 161 and reflective surface 153 of the dental mirror 151.

Figure 7:
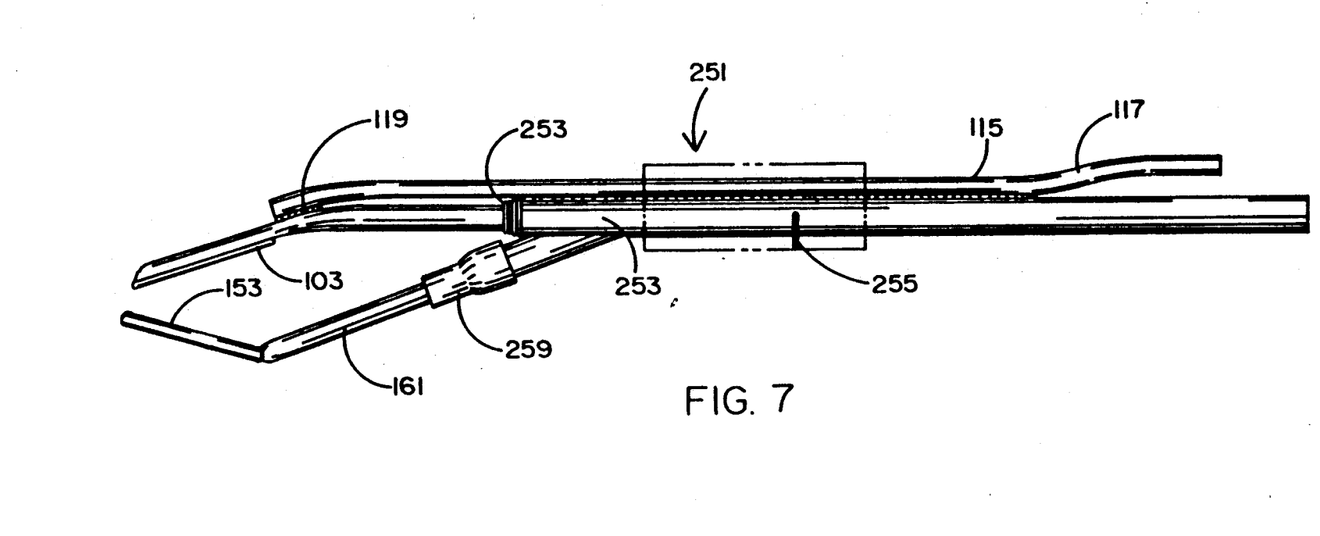
FIG. 7 is a side view of the fiber optic illumination system for dental instruments utilized in conjunction with a combination angled dental mirror-bladed aspirator utilizable in conjunction with the fiber optic illumination system for dental instruments of the present invention.

Referring to FIG. 7, a combination aspirator-swivel mirror instrument 251 is illustrated wherein the mirror portion is swivelable. The bladed retractor 101 which was shown in FIG. 3 is fitted with the cylindrical tube 115 in the same manner as was shown in FIG. 3. Here, the mirror portion, including the reflective surface 153 and extended support 161 does not independently attach to its own main shaft 157, as was the case for FIG. 6, but attaches to a tubular acute T fitting 253. Here, the forward tubular portion 109 of retractor 101 rotatably supports the upper portion of the T of T fitting 253. The bottom portion of the T of T fitting 253, rather than extending downwardly at a right angle, extends forwardly of the retractor 101 at an acute angle. The bottom portion of the T of T fitting 253, also supports the extended support 161, which supports the reflective surface 153.

The upper portion of the T of T fitting 253 is limited in its axial motion along the forward tubular portion 109 of retractor 101 by a forwardly located raised circular land 255 and a rearwardly located raised circular land 257 the silicone band 141 shown in phantom to enable a clear view of land 257. A smaller silicone band of rubber 259 is located at a junction about both the extended support 161, and the bottom portion of the T of the acute T fitting 253 to provide some rotational resistance between these members in order to be able to position the reflective surface 153 in a stable position.

Figure 8:
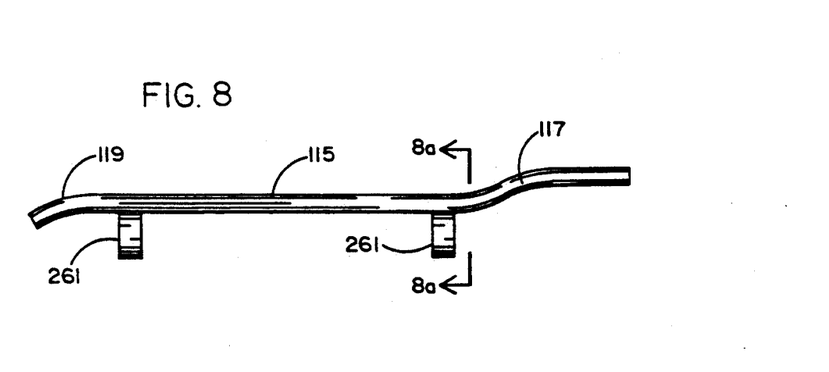
FIG. 8 is a side view of a clip on cylindrical tube utilizable with the fiber optic illumination system for dental instruments of the present invention.
Figure 8A:
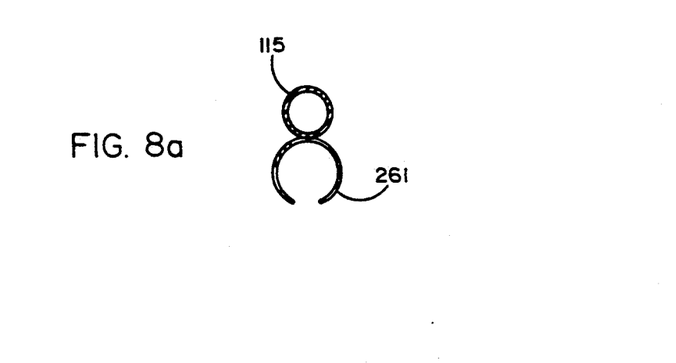
FIG. 8a is a sectional view of the clip-on cylindrical tube taken through line 8a–8b of FIG. 8.

FIG. 8 is a side view of a clip-on style of cylindrical tube 115, which is utilizable with the fiber optic illumination system for dental instruments of the present invention. Cylindrical tube 115 has a pair of clips 261, to assist in holding cylindrical tube 115 onto a tubular shaped support, such as aspirators 51 or 101, or dental mirror 151. In FIG. 8, the cylindrical tube 115 is also illustrated with the "s" bend 117, and a slight bend 119 which were shown in FIG. 3, however, any shape is available for cylindrical tube 115 which is compatible with the configuration of the instrument on which it fits.

Although the invention has been described with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed is:

1. A fiber optic illuminator for a dental instrument comprising:
    an elongate rigid dental instrument;
    a cylindrical tube, attached to said dental instrument, and having a first end and a second end;
    light source means for producing visible light;
    a polymethyl methacrylate optical fiber, having a high refractive index core and a low refractive index cladding, and having a first end connected to said light source means and a second end carried freely within said cylindrical tube, slidably entering at said first end and extending to a point near said second end.

2. The fiber optic illuminator for a dental instrument as recited in claim 1 wherein said dental instrument is an aspirator.

3. The fiber optical illuminator for a dental instrument as recited in claim 2 wherein said aspirator further comprises:
    a rearward tubular portion fittable to a vacuum hose;

a forward tubular portion having a first end attached to said rearward tubular portion and a second end; and a tip end attached to said second end of said forward tubular portion, and terminating in an opening, and wherein said opening has an axis which is angled with respect to an axis of said tip end.

4. The fiber optic illuminator for a dental instrument as recited in claim 3 and further comprising:
a vacuum source;
a length of suction tubing having a first end connected to said vacuum source, and a second end connected to said rearward tubular portion; and
a fitting further comprising:
at least one retainer ring, each having a central bore carrying a portion of said length of suction tubing, and an offset bore carrying a portion of said optical fiber.

5. The fiber optic illuminator for a dental instrument as recited in claim 1 wherein said dental instrument is a mirror.

6. The fiber optic illuminator for a dental instrument as recited in claim 5 wherein said mirror further comprises:
a pair of lands attached, at their outer periphery, to said cylindrical tube;
a main shaft carried by said pair of lands;
an extended support having a first end attached to said main shaft, and a second end;
a reflective surface portion, attached to said second end of said extended support and wherein said main shaft, said extended support, and said reflective surface portion are rotatable with respect to said pair of lands and said cylindrical tube.

7. The fiber optic illuminator for a dental instrument as recited in claim 1 wherein said dental instrument is a combination aspirator-mirror.

8. The fiber optic illuminator for a dental instrument as recited in claim 7 wherein said aspirator-mirror further comprises:
a rearward tubular portion fittable to a vacuum hose;
a forward tubular portion having a first end attached to said rearward tubular portion and a second end;
a tip end attached to said second end of said forward tubular portion, and terminating in an opening, and wherein said forward tubular portion, rearward tubular portion and said tip end lie adjacent to one side of said cylindrical tube;
a pair of lands attached, at their outer periphery, to the other side of said cylindrical tube;
a main shaft carried by said pair of lands;
an extended support having a first end attached to said main shaft, and a second end; and
a reflective surface portion, attached to said second end of said extended support and wherein said main shaft, said extended support, and said reflective surface portion are rotatable with respect to said pair of lands and said cylindrical tube.

9. The fiber optic illuminator for a dental instrument as recited in claim 1 wherein said dental instrument is a combination aspirator-retractor.

10. The fiber optic illuminator for a dental instrument as recited in claim 9 wherein said aspirator-retractor further comprises:
a rearward tubular portion fittable to a vacuum hose;
a forward tubular portion having a first end attached to said rearward tubular portion and a second end;
a tip end attached to said second end of said forward tubular portion, and terminating in an opening, and wherein said opening has an axis which is angled with respect to an axis of said tip end, and wherein said cylindrical tube lies adjacent one side of said tip end; and
a blade, attached to the other side of said top end, and used for retracting tissue.

11. The fiber optic illuminator for a dental instrument as recited in claim 1 wherein said dental instrument is a combination retractor-mirror.

12. The fiber optic illuminator for a dental instrument as recited in claim 11 wherein said retractor-mirror further comprises:
a rearward tubular portion fittable to a vacuum hose;
a forward tubular potion having a first end attached to said rearward tubular portion and a second end;
a tip end attached to said second end of said forward tubular portion, and terminating in an opening, and wherein said opening has an axis which is angled with respect to an axis of/said tip end, and wherein said forward tubular portion, rearward tubular portion and said tip end lie adjacent to one side of said cylindrical tube;
a blade, attached to the other side of said tip end, and used for retracting soft oral tissue.
a pair of lands attached, at their outer periphery, to the other side of said cylindrical tube;
a main shaft carried by said pair of lands;
an extended support having a first end attached to said main shaft, and a second end; and
a reflective surface portion, attached to said second end of said extended support and wherein said main shaft, said extended support, and said reflective surface portion are rotatable with respect to said pair of lands and said cylindrical tube.

13. The fiber optic illuminator for a dental instrument as recited in claim 11 wherein said retractor-mirror further comprises:
a tubular portion having a first end fittable to a vacuum hose, and a second end;
a tip end attached to said second end of said tubular portion, and terminating in an opening, and wherein said opening has an axis which is angled with respect to an axis of/said top end, and where said forward tubular potion, rearward tubular portion and said top end lie adjacent to one side of said cylindrical tube;
a blade, attached to the other side of said tip end, and used for retracting soft oral tissue.
a first circular land, on said tubular portion nearer said top end;
a second circular land, on said tubular portion and spaced apart from said first circular land;
a tubular T fitting having an upper portion surrounding and rotatable with respect to said tubular portion, and a lower portion, said tubular T fitting axially between and axially bounded by said first and second circular lands.
an extended support having a first end attached to said lower portion of said tubular T fitting, and a second end; and
a reflective surface portion, attached to said second end of said extended support and wherein said extended support and said reflective surface portion are rotatable with respect to said tubular portio.

14. The fiber optic illuminator for a dental instrument as recited in claim 1 wherein said cylindrical tube is one of either 11 or 12 gauge hypodermic tubing.

15. The fiber optic illuminator for a dental instrument as recited in claim 1 further comprising at least one clip, supported by said cylindrical tube and wherein said cylindrical tube is clipped to said dental instrument.

16. The fiber optic illuminator for a dental instrument as recited in claim 1 wherein said polymethyl methacrylate optical fiber is covered with a protective sheath, and said second end of said polymethyl methacrylate optical fiber carried within said cylindrical tube is stripped of said protective sheath.

17. A process for providing sterilizeable fiber optic illumination in cooperation with a dental instrument comprising the steps of:

providing an elongate rigid dental instrument having a cylindrical tube, attached to said dental instrument, and having a forward end and a rearward end;

inserting a first end of an optical fiber into said rearward end of said cylindrical tube, said optical fiber having a second end connected to a light source;

energizing said light source to produce visible light from said forward end of said cylindrical tube;

performing dental treatment utilizing said rigid dental instrument and said attached cylindrical tube carrying said first end of said optical fiber;

removing said first end of said optical fiber from said cylindrical tube;

sterilizing said first end of said optical fiber by immersion sterilizing solution;

sterilizing said rigid dental instrument and said attached cylindrical tube in a conventional manner.

18. The process for providing sterilizeable fiber optic illumination in cooperation with a dental instrument as recited in claim 17 wherein said conventional manner further includes autoclaving.

19. The process for providing sterilizeable fiber optic illumination in cooperation with a dental instrument as recited in claim 17 wherein said sterilizing solution is a glutaraldehyde solution.

20. A process for providing sterilizeable fiber optic illumination in cooperation with a dental instrument comprising the steps of:

providing an elongate rigid dental instrument having a cylindrical tube, attached to said dental instrument, and having a forward end and a rearward end;

slidably inserting a first end of an optical fiber into said rearward end of said cylindrical tube and sliding said first end to a point near the forward end of said tube, said optical fiber having a second end connected to a light source;

energizing said light source to produce visible light from said forward end of said cylindrical tube;

performing dental treatment utilizing said rigid dental instrument and said attached cylindrical tube carrying said first end of said optical fiber;

removing said first end of said optical fiber from said cylindrical tube;

discarding said optical fiber; and sterilizing said rigid dental instrument and said attached cylindrical tube in a conventional manner.

* * * * *